United States Patent
Vennard et al.

(10) Patent No.: US 9,539,040 B2
(45) Date of Patent: Jan. 10, 2017

(54) LOCKING AND LAGGING BONE SCREWS

(71) Applicant: DePuy Synthes Products, Inc., Raynham, MA (US)

(72) Inventors: Daniel Vennard, Landenberg, PA (US); William Miller, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/716,280

(22) Filed: May 19, 2015

(65) Prior Publication Data
US 2015/0250516 A1 Sep. 10, 2015

Related U.S. Application Data (63) Continuation of application No. 13/678,813, filed on Nov. 16, 2012, now Pat. No. 9,060,821.

(51) Int. Cl.
*A61B 17/86* (2006.01)
*A61B 17/80* (2006.01)
*A61B 17/84* (2006.01)

(52) U.S. Cl.
CPC ....... *A61B 17/8685* (2013.01); *A61B 17/8052* (2013.01); *A61B 17/8057* (2013.01); *A61B 17/844* (2013.01); *A61B 17/863* (2013.01); *A61B 17/8605* (2013.01); *A61B 17/8615* (2013.01)

(58) Field of Classification Search
CPC .............. A61B 17/844; A61B 17/8685; A61B 17/8057
See application file for complete search history.

(56) References Cited

U.S. PATENT DOCUMENTS

| | | | |
|---|---|---|---|
| 5,520,690 A | 5/1996 | Errico et al. | |
| 5,531,746 A | 7/1996 | Errico et al. | |
| 5,827,285 A | 10/1998 | Bramlet | |
| 7,637,928 B2 | 12/2009 | Fernandez | |
| 8,187,276 B1 | 5/2012 | Zahiri et al. | |
| 8,262,708 B2 | 9/2012 | Michelson | |
| 8,343,196 B2 | 1/2013 | Schneider | |
| 8,574,268 B2 | 11/2013 | Chan et al. | |
| 8,758,346 B2 | 6/2014 | Koay et al. | |
| 8,845,698 B2 | 9/2014 | Schneider | |

(Continued)

FOREIGN PATENT DOCUMENTS

| | | |
|---|---|---|
| EP | 1046376 | 10/2000 |
| WO | WO 2004/069031 | 8/2004 |
| WO | WO 2014/078289 | 5/2014 |

OTHER PUBLICATIONS

U.S. Appl. No. 60/955,506, filed Aug. 13, 2007, Chan et al.

(Continued)

*Primary Examiner* — Andrew Yang
(74) *Attorney, Agent, or Firm* — Baker & Hostetler LLP (57) ABSTRACT

A locking and lagging bone screw. The screw includes a head having an outer surface which is at least partially threaded and a shaft which is at least partially threaded having a first end coupled to the head and a second end adapted to be fastened to bone. The head of the screw is able to rotate independently of the shaft. Thus, the head of the screw can be locked to a bone plate by using a first driver (e.g., a torx driver) and the plate can be lagged to the bone by using a second driver (e.g., a hex driver).

21 Claims, 8 Drawing Sheets

(56) References Cited

U.S. PATENT DOCUMENTS

| | | |
|---|---|---|
| 8,852,245 B2 | 10/2014 | Schneider |
| 8,876,873 B2 | 11/2014 | Schneider |
| 9,060,821 B2 | 6/2015 | Vennard et al. |
| 2002/0128654 A1 | 9/2002 | Steger et al. |
| 2005/0143735 A1 | 6/2005 | Kyle |
| 2006/0229618 A1 | 10/2006 | Dube |
| 2010/0076496 A1 | 3/2010 | Fernandez |
| 2010/0094357 A1 | 4/2010 | Wallenstein et al. |
| 2010/0249781 A1 | 9/2010 | Haidukewych et al. |
| 2010/0312286 A1 | 12/2010 | Dell'Oca |
| 2011/0082506 A1 | 4/2011 | Lore et al. |
| 2011/0106172 A1* | 5/2011 | Wallenstein ....... A61B 17/8685 606/286 |
| 2011/0224735 A1 | 9/2011 | Pagano |
| 2012/0177462 A1* | 7/2012 | Fritzinger ............ A61B 17/861 411/413 |
| 2014/0180345 A1 | 6/2014 | Chan et al. |
| 2015/0018889 A1 | 1/2015 | Schneider |

OTHER PUBLICATIONS

U.S. Appl. No. 61/000,907, filed Oct. 30, 2007, Koay et al.
U.S. Appl. No. 61/084,281, filed Jul. 29, 2008, Fernandez et al.
U.S. Appl. No. 61/242,102, filed Sep. 14, 2009, Koay et al.

* cited by examiner

LOCKING AND LAGGING BONE SCREWS

CROSS REFERENCE TO RELATED APPLICATIONS

This application is a continuation of U.S. patent Ser. No. 13/678,813, filed Nov. 16, 2012, the disclosure of which is hereby incorporated herein by reference in its entirety.

TECHNICAL FIELD

The present invention relates generally to bone screws and, in particular, to bone screws capable of both locking to a plate and lagging the bone to the plate.

BACKGROUND OF THE INVENTION

It is current practice in orthopedic surgery to use plating systems for joining portions of a broken bone or for fusion of portions of separate bones. Such systems are composed essentially of plates and screws for aligning and holding the bone portions in a desired position relative to one another. Plating systems have usefulness in the spine, and have general skeletal use on the flat bones, such as the scapula and the pelvis, by way of example, and for use on tubular bones, such as the humerus, ulna, radius, femur, and tibia, by way of example.

Plates are usually provided to the surgeon for use in sets having a range of sizes so as to provide for such features as biological variability in size, the numbers of segments to be joined, and the length of the portions of bone to be joined. By way of example, a plating system for use on the anterior cervical spine may be used for joining from two to five vertebrae.

Problems associated with such plating systems have included, but are not limited to, an inability to gain adequate fixation and a failure to obtain solid bone healing where the plate will not allow the bone portions to come together over time. These occurrences may cause problems, be associated with surgical failure, and require further surgical procedures to repair the damage, remove the failed hardware, reattempt skeletal stabilization, and the like.

Although the plates may theoretically allow for proper alignment of the vertebrae and their rigid fixation, their use may be restricted by the types of screws available to the surgeon. Typical screws can only perform a single function, for example, lagging or locking. Lagging screws help to achieve anatomical correction whereas locking screws help to achieve more stable constructs. The head of a lagging screw is typically an external hex, and the lagging screw is used to lag two components (such as two bones or bone pieces, or a bone and a plate) together.

Figure 1A:
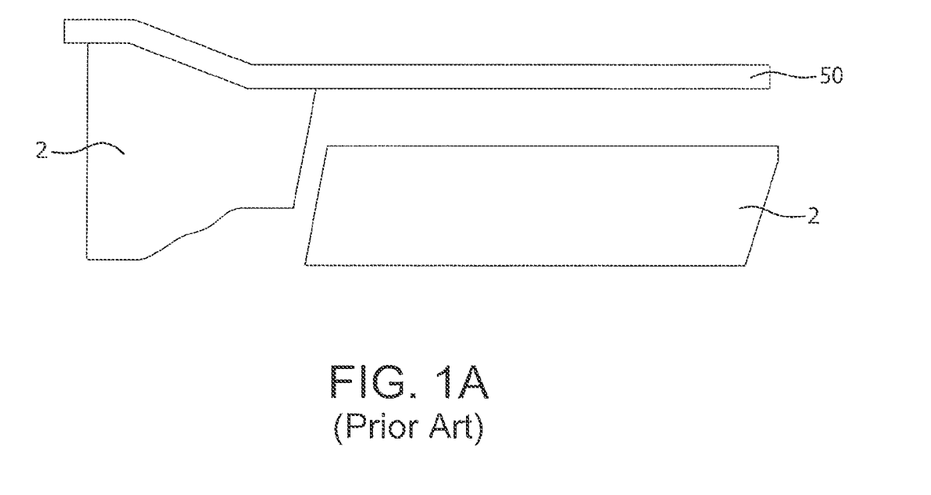
FIG. 1A shows a graphic representing two separate bones and a plate.
Figure 1B:
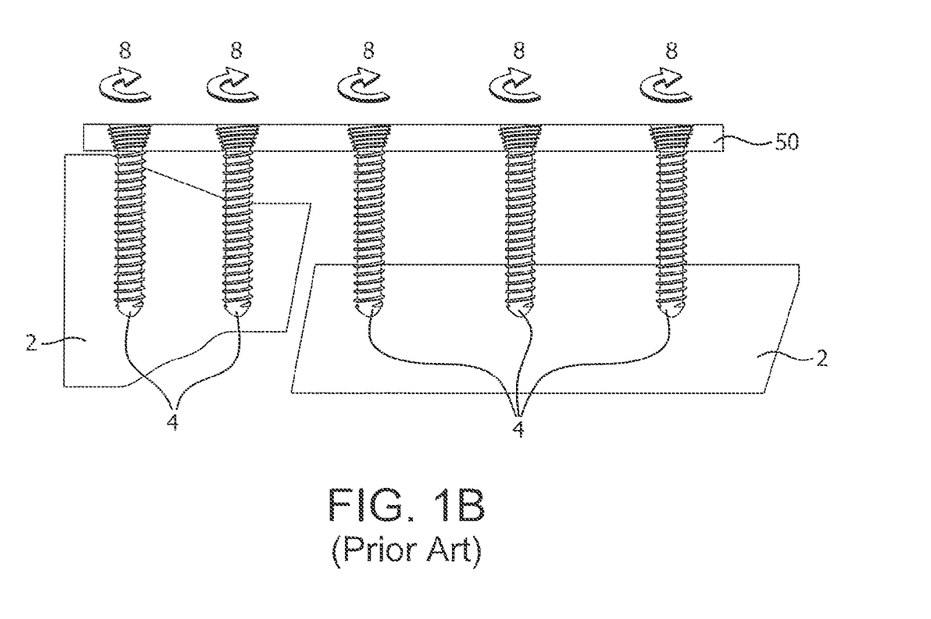
FIG. 1B shows a graphic representing use of locking screws with the bones and plate of FIG. 1A.
Figure 1C:
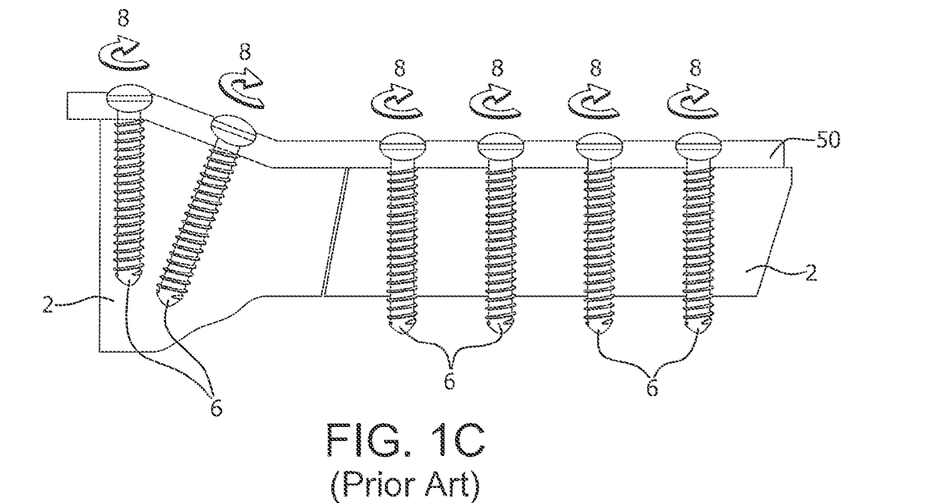
FIG. 1C shows a graphic representing use of lagging screws with the bones and plate of FIG. 1A.
Figure 1D:
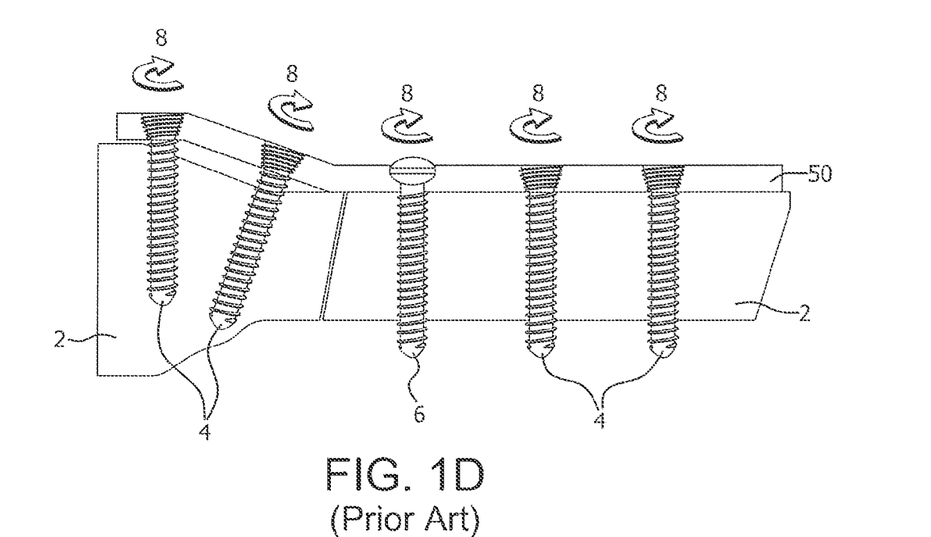
FIG. 1D shows a graphic representing use of some combination of locking screws and lagging screws with the bones and plate of FIG. 1A.

FIGS. 1A, 1B, 1C, and 1D depict the types of problems that may be encountered based on the screw limitations. FIG. 1A shows a graphic representing a fractured bone 2 or two separate bones 2 and a plate 50 extending across the broken or separated portion. In FIG. 1B, locking bone screws 4 are used and rotated or tightened using a rotation 8. The locking bone screws 4 provide for a rigid connection with the plate 50, but it is difficult to achieve anatomical reduction and restore functional anatomical relationships between the bones 2. As is evident, the locking bone screws 4 are insufficient to correct the relationship between the bones 2. In FIG. 1C, lagging bone screws 6 are used and rotated or tightened using a rotation 8. The lagging bone screws 6 provide for anatomical reduction and fixation to restore function anatomical relationships, but the lagging bone screws 6 do not provide stable fixation of the screws 6 to the plate 50. In other words, the fracture of the bone 2 does not receive adequate stability by rigid fixation or splintage to the plate 50. In order to combat this problem, the plate 50 typically requires some combination of both locking bone screws 4 and lagging bone screws 6. FIG. 1D depicts this situation where a lagging screw 6 is used to help reduce the fracture and achieve anatomical reduction, and locking screws 4 are used to provide fixed-angle stability. This solution adds complexity for the surgeon, however, in requiring different types of screws 4, 6 and not all of the screws 4, 6 lock and lag the plate 50 to the bone 2.

There remains a need, therefore, for an improved plating system. In particular, it would be beneficial to provide a single screw capable of locking each and every bone screw to the plate, and a single screw capable of lagging each and every bone screw to the bone.

SUMMARY OF THE INVENTION

To meet these and other needs, and in view of its purposes, the present invention provides for a bone screw capable of locking each and every bone screw to the plate and capable of lagging each and every bone screw to the bone. The locking and lagging bone screw in accordance with the present invention includes a head and shaft where the head of the screw is able to rotate independently of the screw shaft. Thus, the head may include a locking taper feature to lock the head of the screw to the plate. In addition, if the plate needs to be lagged or compressed on the bone, the bone screw could be rotated (even if the screw is already previously locked to the plate) to pull the bone towards the plate and provide the proper anatomical relationships between the bones.

In one embodiment, the present invention provides a locking and lagging bone screw comprising a head having an outer surface which is at least partially threaded, and a shaft having a first end coupled to the head and a second end adapted to be fastened to bone where the shaft is at least partially threaded. The head of the screw is adapted to rotate independently of the shaft.

The head may be coupled to the shaft using any suitable equipment and techniques known in the art so long as the head and shaft are each able to rotate independent of one another. In one embodiment, the head is coupled to the shaft with a screw. In another embodiment, the first end of the shaft comprises a lip which is recessed in the head in order to couple the shaft to the head. The shaft may also contain a fastener, such as a weld or a pin, to prevent the shaft from separating from the head.

The head is rotatable by a first driver and the shaft is rotatable by a second driver. For example, the head includes a first cavity provided to accommodate the first driver and a second cavity provided to accommodate the second driver. The first and second cavities are selected so that each is independently a hexagonal cavity, a six-point star-shaped cavity, a slot, a crossed recess, or the like. Thus, the cavities can accommodate a torx driver, a hex driver, a socket driver, or the like, as the first and second drivers. In an exemplary embodiment, the first driver is a torx driver and the second driver is a hex driver. In an alternative embodiment, the first driver and second driver are each the same type of driver (e.g., both the first and second drivers are torx drivers) having different or varying sizes (e.g., one is smaller or bigger than the other).

The shaft of the screw has a first end coupled to the head and a second end adapted to be fastened to bone. The first end of the shaft may be of any suitable shape (e.g., substantially flat, rounded, curved, or the like). The second end of the shaft may be blunt or sharp and pointed. In one embodiment, the screw is self-tapping. The shaft of the screw may be fully or partially threaded. In one embodiment, the shaft comprises a first and second thread type and the head comprises a third thread type. In another embodiment, the shaft comprises a first cortical inner core diameter proximate the first end, a transition, and a second cortical inner core diameter extending from the transition to the second end.

The head and the shaft may be aligned along a central longitudinal axis. In the alternative, the head may be rotatable along a variable or fixed angle relative to the shaft.

In another embodiment, the present invention provides a plate and screw assembly comprising a plate and at least one locking and lagging bone screw. The plate may include an upper surface and a lower surface and at least one through hole having a wall extending from the upper surface to the lower surface where the wall of the through hole is at least partially grooved. The locking and lagging bone screw includes a shaft and a head being freely rotatable independent of the shaft. The shaft has a first end coupled to the head and a second end adapted to be fastened to bone. The shaft and the head are each at least partially threaded. The locking and lagging bone screw or screws includes or include a locking feature when the head is threaded to the grooved wall of the hole, and the screw includes a lagging feature when the shaft is rotated or screwed into the bone.

The plate assembly may include one or two of the locking and lagging bone screws and at least one screw of a different type. For example, the plate may include one or two of the locking and lagging bone screws and one or two screws having a locking function only. The plate may include any suitable type and configuration of through holes including a combi-hole. In one embodiment, the through hole is a conical screw hole allowing for ±5° of angulation during screw insertion.

In yet another embodiment, the present invention provides a kit comprising a plurality of locking and lagging bone screws where each of the plurality of screws comprises a different configuration, size, or driver type. The kit may further contain traditional locking screws of varying sizes and the different driver types.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

The present invention provides for a bone screw with a head that is able to rotate independently of the remainder of the screw. The screw includes a locking feature where the screw is locked to a plate and, in particular, the head of the screw is locked to the plate. In addition, if the plate needs to be lagged or compressed on the bone, the screw includes a lagging feature where the screw could be rotated (even if already locked to the plate) to pull the bone and the plate together.

As used in this document, the term "locked" or "locking" means the screw and, in particular, the head of the screw is locked to the plate, and the screw cannot back out. The term "lagged" or "lagging" means the shaft of the screw is capable of movement to allow bone portions to move closer together, closer to the plate, or both even if the head of the screw is locked to the plate. Thus, a locking and lagging bone screw in accordance with the present invention is permitted to move relative to the plate even after being locked to the plate when a force is provided against the screw.

Figure 2:
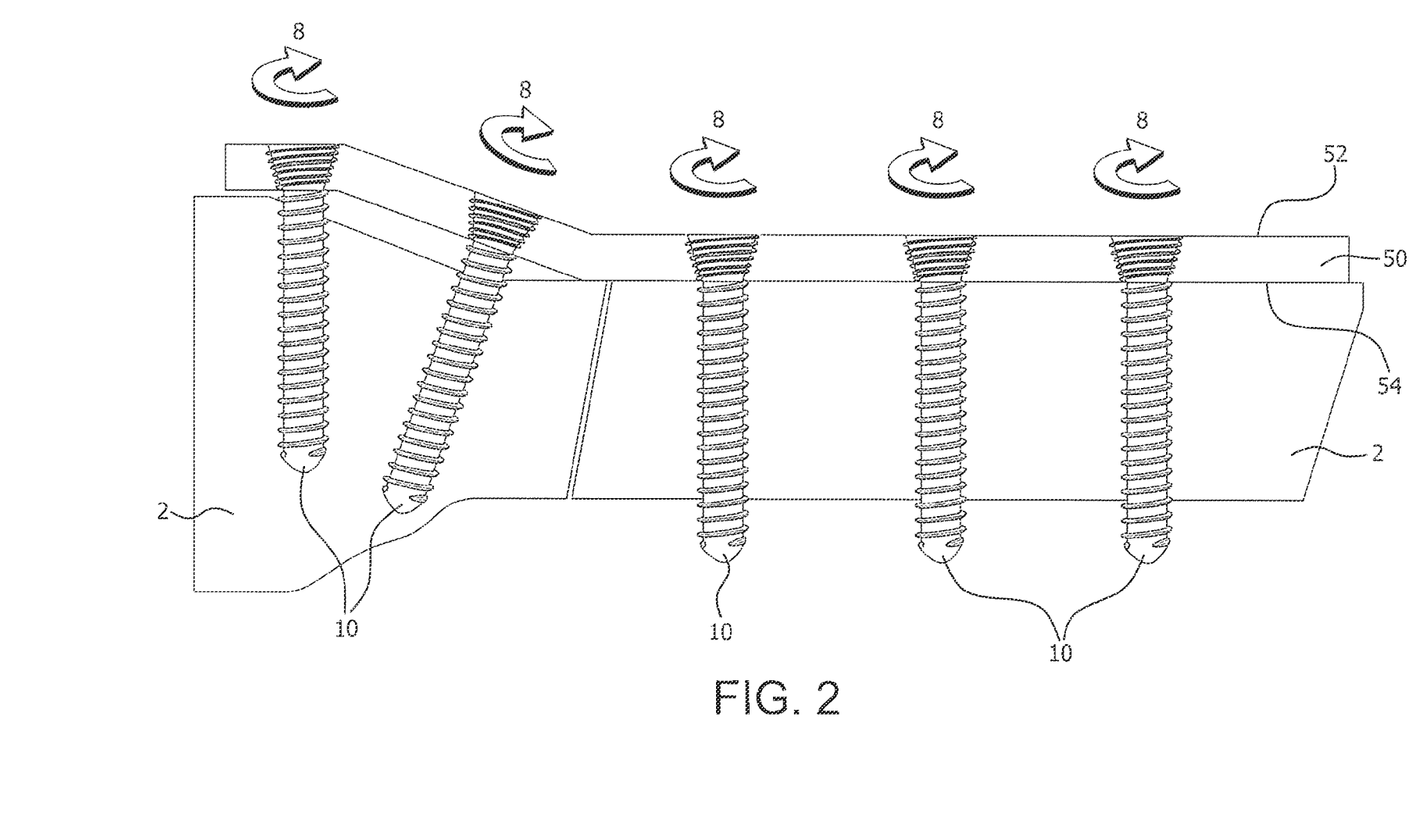
FIG. 2 shows a graphic representing use of locking and lagging screws in accordance with the present invention with the bones and plate of FIG. 1A.
Figure 3:
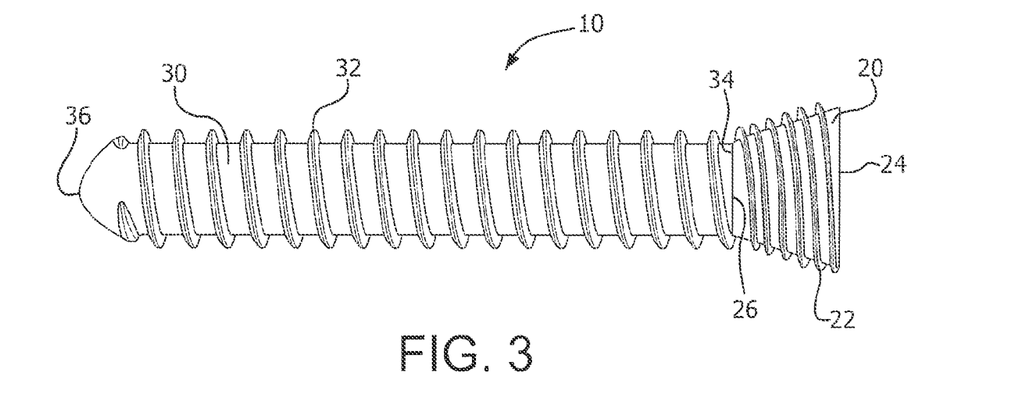
FIG. 3 shows a screw according to an embodiment of the present invention including both locking and lagging functions.

Referring now to the drawing, in which like reference numbers refer to like elements throughout the various figures that comprise the drawing, each locking and lagging bone screw 10 includes a head 20 and a shaft 30. As best shown in FIG. 2, each locking and lagging bone screw 10 is able to lag a plate 50 to the bone 2 and is able to lock directly to the plate 50 through rotation 8 of each screw 10. In other words, the head 20 and the shaft 30 rotate independent and irrespective of one another so that the head 20 can lock to the plate 50 and the shaft 30 can lag to the bone 2. As depicted in FIG. 3, the head 20 of the screw 10 includes a first end 24 and a second end 26, and the shaft 30 includes a first end 34 and a second end 36. The first end 34 of the shaft 30 is coupled to the second end 26 of the head 20 and the second end 36 of the shaft 30 is adapted to be fastened to the bone 2.

Figure 4:
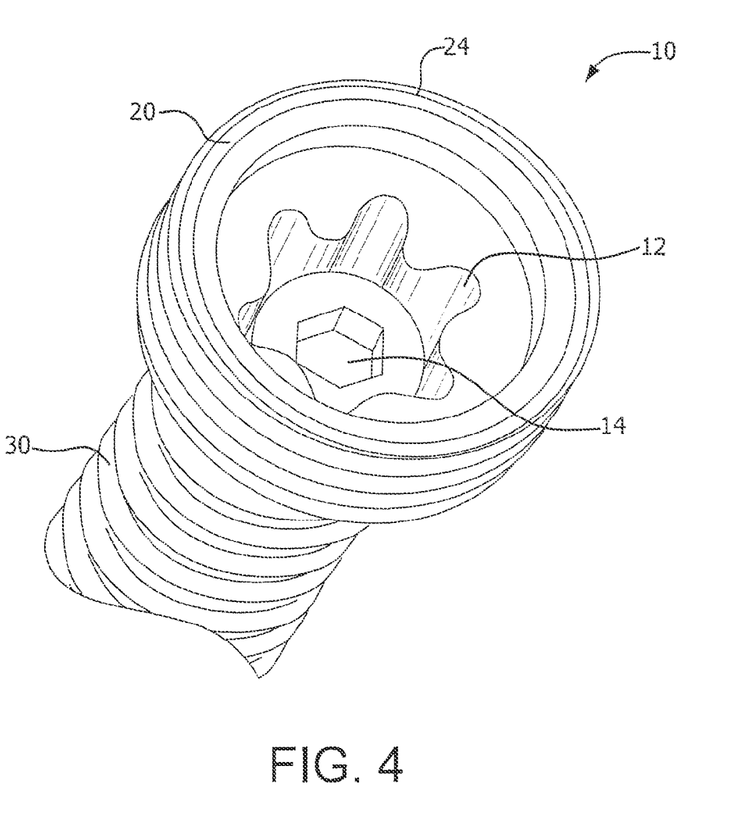
FIG. 4 shows the head portion of a locking and lagging screw according to an embodiment of the present invention.
Figure 5:
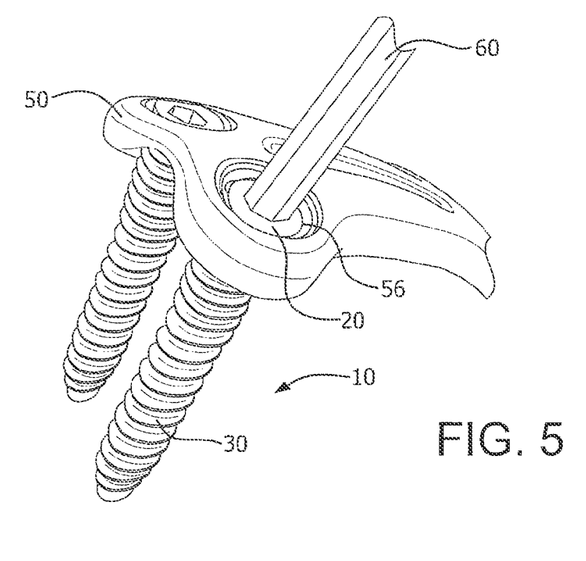
FIG. 5 shows a plate using two locking and lagging screws in accordance with the present invention and locking the screw to the plate with a first driver.
Figure 6:
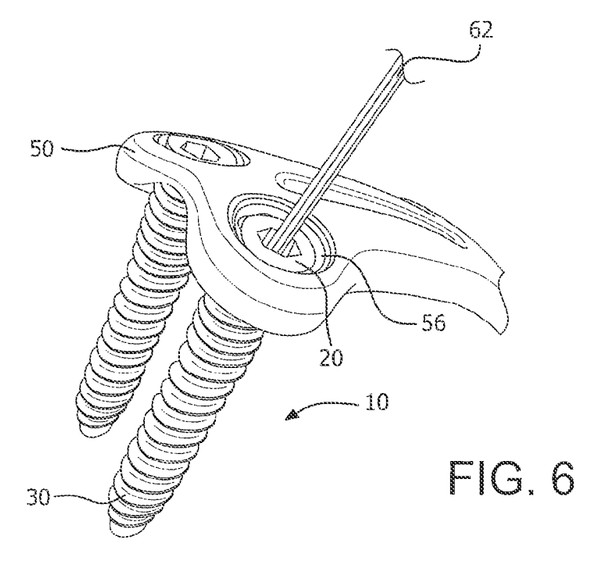
FIG. 6 shows the embodiment depicted in FIG. 5 and the ability to lag the screws with a second driver.

The head 20 of the screw 10 is adapted to rotate independently of the shaft 30. As shown in FIGS. 5 and 6, the head 20 is rotatable by a first driver 60 and the shaft 30 is rotatable by a second driver 62. The first end 24 of the head 20 should be sized and configured to accept the first driver 60 and the second driver 62, respectively. Any suitable configuration and type of head 20 may be selected so long as the head 20 and the shaft 30 may each be rotated independent of one another. In other words, rotating the head 20 does not rotate the shaft 30 and rotating the shaft 30 does not rotate the head 20. For example, the head 20 includes at least one cavity within its first end 24. With emphasis on FIG. 4, the head 20 may include a first cavity 12 provided to accommodate the first driver 60 and a second cavity 14 provided to accommodate the second driver 62.

Each cavity may be selected by one of ordinary skill in the art, for example, based on the desired torque, appropriate fit between the cavity and the drivers 60, 62, and in order to cause minimal damage to the head 20 and to the drivers 60, 62. In an exemplary embodiment, the first and second cavities 12, 14 are selected so that each is independently a hexagonal cavity, a six-point star-shaped cavity, a slot, a crossed recess, or the like. The first and second cavities 12, 14 are preferably different from one another. For example, as shown in FIG. 4, the first cavity 12 may be a six-point star-shaped cavity and the second cavity 14 may be a hexagonal cavity or vice versa. It is also envisioned, however, that the first and second cavities 12, 14 may be of the same type, but of a different size. In other words, the first cavity 12 may be a six-point star-shaped cavity and the second cavity 14 may also be a six-point star-shaped cavity (shown in FIG. 9), but the first cavity 12 has a larger radius than the second cavity 14.

The cavities 12, 14 may be sized to accommodate the appropriate and corresponding driver 60, 62. A typical hand driver 60, 62 often includes a cylindrical handle of a size and shape suitable for a human hand, an axial shaft fixed to the handle, and a tip of the axial shaft which is shaped to fit a particular type of screw head 20. The driver 60, 62 may include a tip, which is capable of applying torque to either the head 20 or the shaft 30 of the screw 10 by rotating the tip of the driver 60, 62. For example, the cavities 12, 14 may accommodate a torx driver in the case of a six-point star-shaped cavity, a hex driver in the case of a hexagonal cavity, a socket driver, or the like. Torx head sizes are described using the capital letter "T" followed by a number where a smaller number corresponds to a smaller point-to-point dimension of the screw head 20. Common sizes include T10, T15, and T25.

In the embodiment shown in FIG. 4 where the first cavity 12 is a six-point star-shaped cavity and the second cavity 14 is a hexagonal cavity, the first driver 60 is a torx driver and the second driver 62 is a hex driver. For example, the first driver 60 for turning the head 20 is a torx driver (e.g., size T25) and the second driver 62 for turning the shaft 30 is a hex driver. In the embodiment where the first driver 60 and the second driver 62 are each the same type of driver (e.g., both the first and second drivers 60, 62 are torx drivers), each driver has a different or varying size. In other words, one driver 60, 62 is smaller or bigger than the other driver 60, 62 (e.g., the first driver 60 is a T25 and the second driver is a T10 or vice versa). One of ordinary skill in the art could select the appropriate driver 60, 62 based on the size and type of cavities 12, 14 provided in the first end 24 of the head 20.

The head 20 of the screw 10 may be of any suitable size and shape. For example, the head 20 may be conical, oval, bugle, or the like. Preferably, the head 20 is of a conical shape meaning that the first end 24 of the head 20 has a greater or larger diameter than the second end 26 of the head 20. The head 20 is preferably sized and shaped to recess within the hole of the plate 50 such that the top surface or first end 24 of the head 20 is substantially flush and coplanar with the upper surface of the plate 50. In the alternative, the head 20 may be recessed within or below the upper surface of the plate 50. It is desired, however, that the head 20 of the screw 10 does not protrude beyond any outer surface or upper surface of the plate 50.

The head 20 of the screw 10 includes an outer surface which is at least partially threaded 22 along its length from the first end 24 to the second end 26 of the head 20. In other words, the head 20 includes an external thread 22, which is capable of engaging a corresponding groove in one or more holes within the plate 50. The external thread 22 may continue along the entire distance from the first end 24 to the second end 26 of the head 20 or along some portion of the distance from the first end 24 to the second end 26 of the head 20 (e.g., only proximate the first end 24). The type of thread, including the spacing, diameter, and pitch, is not especially restricted and may be selected by one of ordinary skill in the art. Preferably, the thread 22 should be sized and configured to be received within the corresponding groove of the holes in the plate 50.

The shaft 30 of the screw 10 has a first end 34 coupled to the head 20. The first end 34 of the shaft 30 may be of any suitable size and shape. For example, the first end 34 may be substantially flat, rounded, spherical, or provided in some other suitable shape known in the art. Preferably, the first end 34 of the shaft 30 is substantially flat and coplanar with the second end 26 of the head 20. The shaft 30 may be coupled to the head 20 using any suitable mechanisms and techniques known in the art so long as the head 20 and the shaft 30 are each able to rotate independent and separate from one another.

For example, the head 20 and the shaft 30 may be coupled together using a screw, a bolt, or some other fastening element known in the art. In a preferred embodiment, the first end 34 of the shaft 30 is coupled to the second end 26 of the head 20 using a screw 80, with a head 82 sized to retain the head 20 of the locking and lagging screw 10 to the shaft 30. Although the first end 34 of the shaft 30 is proximate to the second end 26 of the head 20, there may be a space or gap therebetween to allow for adequate rotation of each of the head 20 and the shaft 30, respectively. Therefore, there may be provided a spacer, washer, or the like, allowing adequate separation between the head 20 and the shaft 30.

Figure 7A:
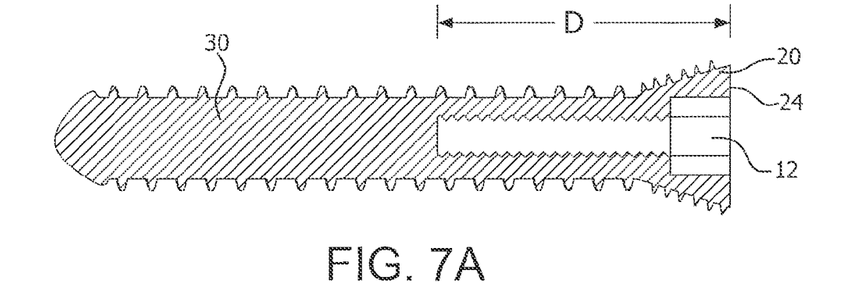
FIGS. 7A-7D show one technique that may be used to create a locking and lagging screw in accordance with the present invention.
Figure 7B:
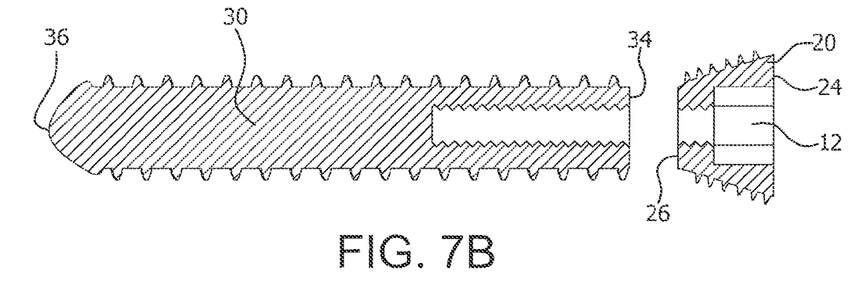
Figure 7C:
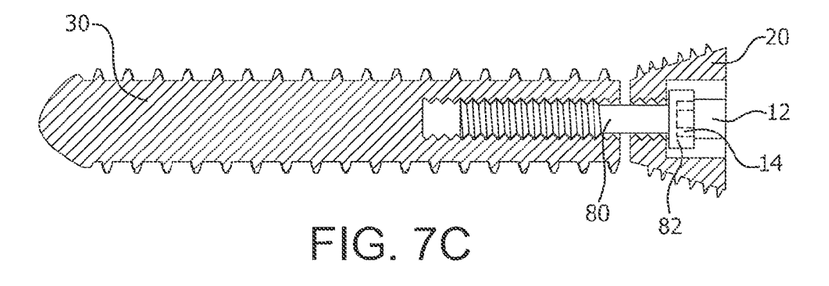
Figure 7D:
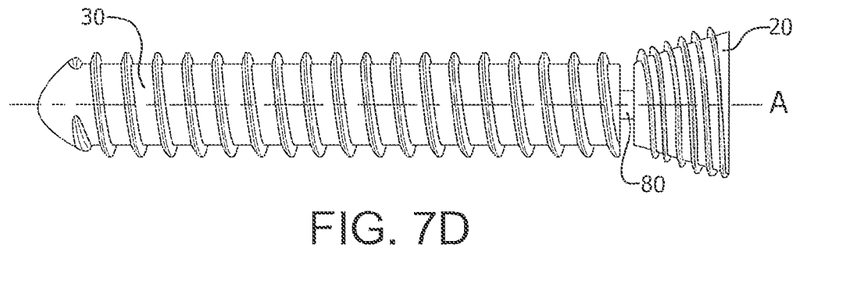

FIGS. 7A-7D show one technique used to create a locking and lagging screw 10 in accordance with the present invention. In FIG. 7A, a standard locking screw is drilled and tapped in the first end 24 of the head 20 a distance D. For example, the screw may be drilled and tapped for an M2 set screw, where the M designations are defined in the international standard ISO 68-1, although any suitable size screw may be selected based on the size of the original locking screw 10. As depicted in FIG. 7B, the screw head 20 is subsequently removed, for example, by cutting along the plane where the head 20 and the shaft 30 meet. This provides a head 20 with a first end 24 and a second end 26 and a shaft 30 with a first end 34 and a second end 36. Then, as shown in FIG. 7C, a smaller screw 80, e.g., the M2 set screw, is inserted into the first end 24 of the head 20 and screwed into the first end 34 of the shaft 30 coupling the head 20 to the shaft 30. The screw 80 may be partially or fully threaded along its length. The head 82 of the screw 80 may be recessed, for example, into the head 20 of the locking and lagging screw 10 such that the original opening 12, sized and configured for the first screw driver 60, is maintained. The screw 80 is not fully tightened, allowing for the head 20 to have a free axis of rotation along a central longitudinal axis A and the shaft 30 to have a free axis of rotation along the central longitudinal axis A. Therefore, as depicted in FIG. 7D, the head 20 and the shaft 30 are each free to rotate irrespective of the other along the central longitudinal axis A.

Figure 8:
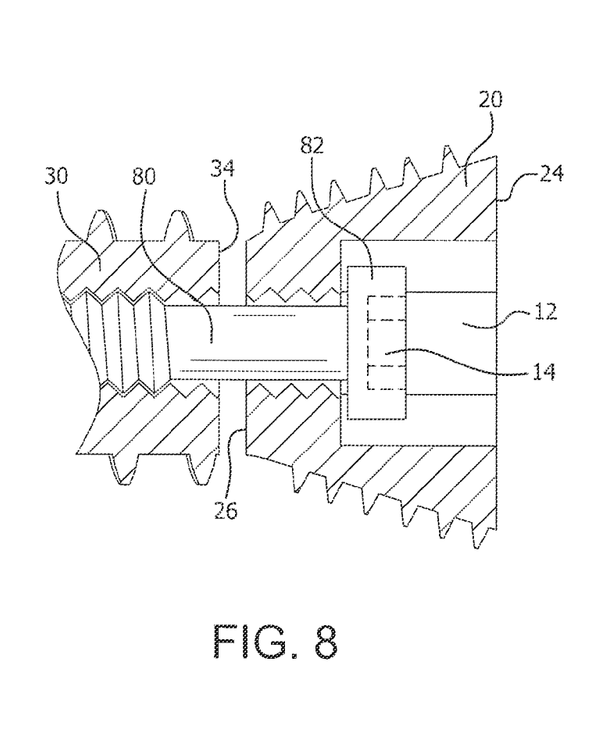
FIG. 8 shows a partial side view of one embodiment of the locking and lagging screw in accordance with the present invention.
Figure 9:
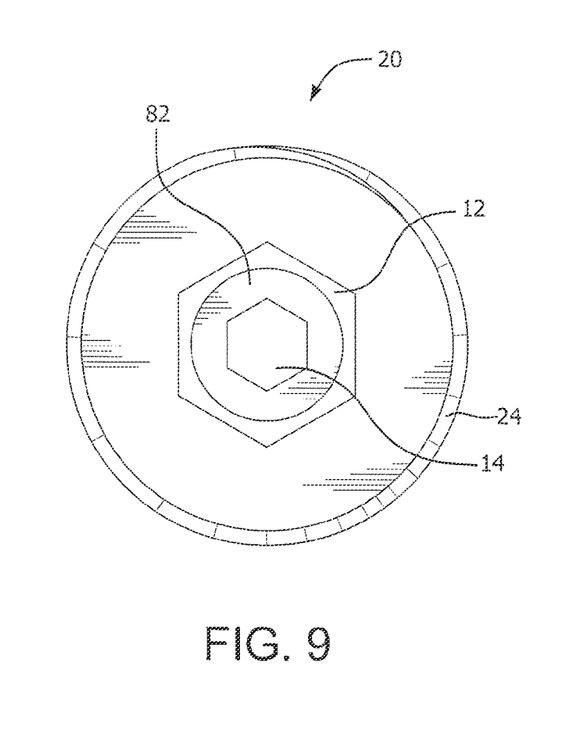
FIG. 9 shows a top view of the locking and lagging screw shown in FIG. 8.

FIG. 8 shows a partial side view of one embodiment of the locking and lagging screw 10, and FIG. 9 shows a top view of the head 20 depicted in FIG. 8. As is evident, the head 82 of the smaller set screw 80 is recessed in the original and first cavity 12 of the locking and lagging screw 10. Therefore, the set screw 80 contains the second cavity 14, which can operate to rotate the shaft 30, but the first cavity 12 of the locking and lagging screw 10 remains accessible and can operate to rotate the head 20 of the locking and lagging screw 10. As shown in FIG. 9, the first cavity 12 and second cavity 14 may each be a hexagonal cavity of different sizes or of other suitable shapes as described in this document.

Figure 10:
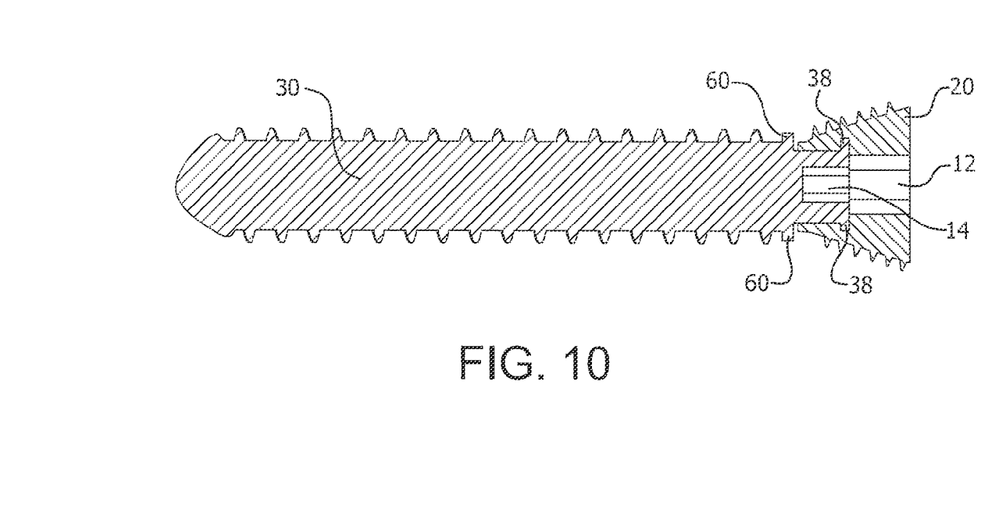
FIG. 10 shows a cross sectional view of an alternative embodiment of the locking and lagging screw in accordance with the present invention.
Figure 11:
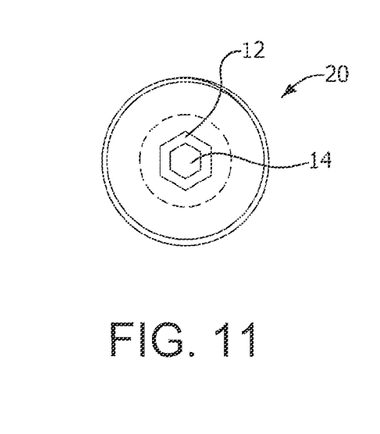
FIG. 11 shows a top view of the locking and lagging screw shown in FIG. 10.

FIG. 10 shows a cross section view of a locking and lagging screw 10 according to an alternative embodiment of the present invention, and FIG. 11 shows a top view of the head 20 depicted in FIG. 10. The first end 34 of the shaft 30 may be provided with, for example, a lip 38, ridge, or the like (e.g., a ring, tabs, or the like) in order for the shaft 30 to be retained inside the head 20. The lip 38 may be machined in or affixed to the shaft 30. If needed, a fastener 60 (e.g., a nut, pin, weld, or the like) may be provided below the head 20 (e.g., proximate the first end 34 of the shaft 30) to keep the shaft 30 from separating from the head 20. In this case, the first end 34 of the shaft 30 contains the second cavity 14, which can operate to rotate the shaft 30, and the first cavity 12 of the locking and lagging screw 10 remains accessible and can operate to rotate the head 20 of the locking and lagging screw 10. As shown in FIG. 11, the first cavity 12 and second cavity 14 may again each be a hexagonal cavity of different sizes or of other suitable shapes as described in this document.

In one embodiment, the locking and lagging screw 10 is pre-assembled prior to surgery. In other words, the head 20 is already coupled to the shaft 30 at the time of surgery (e.g., during the surgical procedure). Therefore, the surgeon does not need to assemble any pieces or parts together during the operation (e.g., the head 20 is not assembled with the shaft 30 at the time of surgery).

The shaft 30 of the screw 10 has a second end 36 adapted to be fastened to the bone 2. The second end 36 of the shaft 30 may be blunt or pointed. FIG. 3 depicts an example of a blunt second end 36. The second end 36 may also be sharp or pointed. In one embodiment, the screw 10 is self-tapping, where the screw 10 has the ability to cut a thread as the screw 10 is driven into the bone 2. Thus, the screws 10 may be directly affixed to the bone 2 or the bone 2 may be pre-drilled in order to accommodate the screws 10, as would be known by one of ordinary skill in the art.

The screw 10 may be of any suitable length and diameter. For example, the screw 10 may have a length including the head 20 and the shaft 30, which may be selected in the range of from about 2 mm to about 90 mm, where 14 mm to 50 mm lengths are available in 2 mm increments and 55 mm to 90 mm lengths are available in 5 mm increments. The outside screw diameter may range from about 1.5 mm to about 6.0 mm, preferably about 4.0 mm to about 5.0 mm, for example.

The shaft 30 of the screw 10 may be fully or partially threaded. The shaft 30 has at least a partial thread along its length from the first end 34 to the second end 36 of the shaft 30. In some embodiments, the shaft 30 is fully threaded along its length from the first end 34 to the second end 36 of the shaft 30. In another embodiment, the shaft 30 has a partial thread from the second end 36 to less than half way (e.g., <50%, preferably, about 33%) along the length of the shaft 30 and a non-threaded portion. The type of thread, including the spacing, diameter, and pitch, is not especially restricted and may be selected by one of ordinary skill in the art. Preferably, the thread should be sized for providing adequate lagging to the bone 2.

In one embodiment, the shaft 30 comprises a first thread type and a second thread type and the head 20 comprises a third thread type. In other words, the spacing, diameter, or pitch is different between the first, second, and third thread types, respectively. In another embodiment, the shaft 30 comprises a first cortical inner core diameter proximate the first end 34 of the shaft 30, a transition, and a second cortical inner core diameter extending from the transition to the second end 36 of the shaft 30. The first cortical inner core diameter may range from about 5.0 mm±0.5 mm and the second cortical inner core diameter may range from about 3.8 mm±0.5 mm, for example, and the transition may vary in diameter changing from the first cortical inner core diameter to the second cortical inner core diameter.

The head 20 and the shaft 30 may be aligned along a single axis or may be provided at some angle relative to one another. For example, both the head 20 and the shaft 30 may be aligned along a central longitudinal axis A as shown in FIG. 7D, where the head 20 and the shaft 30 are each independently rotatable about the central longitudinal axis A. In the alternative, the shaft 30 may be rotatable about the central longitudinal axis A and the head 20 may be rotatable along a variable or fixed angle relative to the shaft 30. In the case of a screw 10 with a variable angle, the head 20 may be comprised of a collet (e.g., a hexagonal collet) and the first end 34 of the shaft 30 may be rounded or spherical in shape in order to be housed within the collet, which provides for angled rotational movement about the central longitudinal axis A. The angle of rotation may range between 0° and 30°, for example. In one embodiment, the first driver 60 for rotating the head 20 or collet is a hex driver and the second driver 62 for rotating the shaft 30 is a torx, e.g., size T25.

In another embodiment, the present invention provides a plate 50 and a screw assembly comprising a plate 50 and at least one locking and lagging bone screw 10. The plate 50 may include an upper surface 52 and a lower surface 54 (see FIG. 2) and at least one through hole having a wall extending from the upper surface to the lower surface where the wall is at least partially grooved. The at least one locking and lagging bone screw 10 includes a shaft 30 and a head 20 being freely rotatable independent of the shaft 30. The locking and lagging bone screw or screws 10 include a locking feature when the head 20 is threaded to the wall having grooves of the hole, and the screw 10 includes a lagging feature when the shaft 30 is rotated or screwed into the bone 2.

The plate 50 may be of any suitable size and shape. The plate 50 may vary in both length and width, but generally the length exceeds the width so as to define a generally longitudinal member. The length of the plate 50 may range from about 50 mm to about 500 mm and the width of the plate 50 may range from about 5 mm to about 18 mm, for example. The thickness of the plate 50 may vary as well from approximately 3 mm to about 5 mm. The plate 50 may be comprised of a dog-bone type shape with four through holes. The upper surface and lower surface of the plate 50 may be substantially flat or may be curved in order to conform with the shape of the bones 2. The holes can be provided perpendicularly to the plate 50 or at some angle relative to the plate 50 as the application requires.

The plate 50 may include any suitable type, number, and configuration of through holes. The holes may be sized to be approximately equal to the size of the head 20. In one embodiment, the through hole is a conical screw hole allowing for ±5° of angulation during screw insertion. In an alternative embodiment, the plate 50 may include one or more combi-holes, for example. The combi-hole is an elongated screw hole including two joined circular sections. One of the circular sections is threaded and adapted to receive a screw with a threaded head (e.g., a locking screw 4) and the other circular section is smooth and adapted to receive a screw with a non-threaded head (e.g., a lagging screw 6). It is contemplated, however, that combi-holes may not be required because a single screw 10 in accordance with the invention is now able to provide both the locking and lagging functions.

The plate 50 may include one or two of the locking and lagging bone screws 10 and at least one screw of a different type. For example, the plate 50 may include one or two of the locking and lagging bone screws 10 and one or two locking screws 4 only capable of performing the locking function. In other words, the plate 50 may require one or two locking and lagging bone screws 10 in order to lag the plate 50 to the bone 2. After the plate 50 is lagged to the bone 2, the remaining screws can be regular or traditional locking screws 4.

In yet another embodiment, the present invention provides a kit comprising a plurality of locking and lagging bone screws 10 where each of the plurality of screws 10 comprises a different configuration, size, or driver type. The kit may further contain traditional locking screws 4 of varying sizes and the different drivers 60, 62 necessary to rotate the head 20 and the shaft 30 of each screw 10, respectively. The kit may be especially useful in trauma environments, for ease of use and simplicity.

The screws 10 and the plate 50 may be composed of any suitable biocompatible materials known in the art. For example, the screw 10, the plate 50, or both may be made of stainless steel, titanium, or a titanium alloy.

Preferred embodiments of the present invention are directed to applications in the spine for anterior plates 50. The preferred embodiments of the screw-and-plate system are not limited to applications or mounting in the anterior spine, however, and may be utilized in the lumbar spine or for mounting to other bones in the human body, as would be apparent to one having ordinary skill in the art.

As depicted in FIG. 2, the locking and lagging screws 10 in accordance with the present invention provide the surgeon the ability to use a single screw to both lock the screw 10 to the plate 50 and lag the bone 2 to the plate 50 (even if the screw 10 is already locked to the plate 50) to pull the bone 2 and the plate 50 together and to obtain proper anatomical reduction.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. A locking and lagging bone screw comprising:
   a shaft elongate along a central axis, the shaft including a first shaft end and a second shaft end opposite the first shaft end along the central axis;
   a head including a first head end and a second head end opposite the first head end, the head configured to be coupled to the shaft such that: 1) the head is rotatable about the central axis independently of the shaft, 2) the first shaft end faces the second head end, and 3) the first shaft end is spaced from the second head end along the central axis by a gap; and
   a connection screw configured to bridge the gap and couple the head to the shaft;
   wherein, when the head and the shaft are in a fully assembled configuration, 1) the connection screw is rotatable relative to the head about the central axis, and 2) the connection screw is the only portion of the locking and lagging screw that bridges the gap.

2. The locking and lagging bone screw of claim 1, wherein the head defines a first cavity, and the connection screw defines a second cavity that is at least one of a different size and a different shape from the first cavity.

3. The locking and lagging bone screw of claim 2, wherein the connection screw includes a connection screw head that defines the second cavity, the connection screw includes a connection screw shaft that includes a threaded outer surface, and the shaft includes a threaded inner surface that defines a hole configured to receive the connection screw shaft.

4. The locking and lagging bone screw of claim 3, wherein the connection screw head is inserted in the first cavity and the connection screw shaft is inserted in the hole.

5. The locking and lagging bone screw of claim 1, wherein the head is rotatable along a variable angle relative to the shaft.

6. The locking and lagging bone screw of claim 1, wherein the shaft includes a threaded outer surface.

7. The locking and lagging bone screw of claim 6, wherein the head includes a threaded outer surface having a pitch that is different than a pitch of the threaded outer surface of the shaft.

8. The locking and lagging bone screw of claim 1, wherein the head includes a threaded outer surface.

9. The locking and lagging bone screw of claim 1, wherein, in the fully assembled configuration, the connection screw is rotatably coupled to the shaft so that rotation of the connection screw causes the shaft to rotate about the central axis.

10. A locking and lagging bone screw comprising:
    a shaft elongate along a central axis, the shaft including a first shaft end and a second shaft end, the first shaft end opposite the second shaft end in a first direction along the central axis;
    a head including a first head end and a second head end opposite the first head end, the head configured to be coupled to the shaft such that: 1) the head is rotatable independently of the shaft about the central axis when the shaft and the head are in a fully assembled configuration, 2) the first shaft end faces the second head end, and 3) the second head end is positioned closer to the first head end with respect to the first direction than any point on the shaft is positioned from the first head end with respect to the first direction.

11. The locking and lagging bone screw of claim 10, further comprising a connection screw coupled to both the shaft and the head such that: 1) a first end of the connection screw is opposite a second end of the connection screw in the first direction and 2) the second end of the connection screw is positioned closer to the second shaft end with respect to the first direction than any point on the head is positioned from the second shaft end with respect to the first direction.

12. The locking and lagging bone screw of claim 10, further comprising a connection screw including a connection screw head and a connection screw shaft, wherein the head defines a cavity configured to receive the connection screw head, and the shaft includes a threaded inner surface that defines a hole configured to receive the connection screw shaft.

13. The locking and lagging bone screw of claim 12, wherein the connection screw head is inserted in the cavity, and the connection screw shaft is inserted in the hole.

14. The locking and lagging bone screw of claim 13, wherein rotation of the connection screw translates the shaft relative to the head in the first direction.

15. The locking and lagging bone screw of claim 10, wherein the head is rotatable along a variable angle relative to the shaft.

16. The locking and lagging bone screw of claim 10, wherein the shaft includes a threaded outer surface.

17. The locking and lagging bone screw of claim 16, wherein the head includes a threaded outer surface having a pitch that is different than a pitch of the threaded outer surface of the shaft.

18. A kit comprising:
 a locking and lagging bone screw including a head, and further including a shaft that is elongate along a longitudinal axis and rotatable relative to the head about the longitudinal axis when the head and the shaft are in a fully assembled configuration;
 a plate including a first surface, a second surface opposite the first surface, and an inner surface that defines a hole that extends from the first surface to the second surface, wherein the plate is configured such that the locking and lagging bone screw is insertable into the hole at a plurality of angles.

19. The kit of claim 18, wherein the head includes an outer surface that is at least partially threaded, the inner surface of the plate is at least partially grooved, and the outer surface is configured to engage with the inner surface to lock the locking and lagging screw at one of the plurality of angles.

20. The kit of claim 18, wherein the inner surface defines a conical shape of the hole.

21. The kit of claim 18, wherein the hole extends from the first surface to the second surface along a central hole axis, and the plurality of angles are measured between the central hole axis and the longitudinal axis.

* * * * *